(12) United States Patent
Brauner

(10) Patent No.: US 7,820,451 B2
(45) Date of Patent: Oct. 26, 2010

(54) ANALYTICAL TEST ELEMENT

(75) Inventor: Michael Brauner, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1033 days.

(21) Appl. No.: 10/959,734

(22) Filed: Oct. 6, 2004

(65) Prior Publication Data

US 2005/0084982 A1 Apr. 21, 2005

(30) Foreign Application Priority Data

Oct. 7, 2003 (DE) ................................ 103 46 417

(51) Int. Cl.
*G01N 21/00* (2006.01)
(52) U.S. Cl. ........................ 436/178; 422/58; 422/61; 422/100
(58) Field of Classification Search ................ 436/169, 436/178; 422/61, 58, 100
See application file for complete search history.

(56) References Cited

U.S. PATENT DOCUMENTS

| 3,473,576 | A | 10/1969 | Amneus |
| 4,312,834 | A | 1/1982 | Vogel et al. |
| 4,323,536 | A | 4/1982 | Columbus |
| 4,477,575 | A | 10/1984 | Vogel et al. |
| 5,104,811 | A | 4/1992 | Berger et al. |
| 5,846,837 | A | 12/1998 | Thym et al. |
| 6,592,815 | B1 | 7/2003 | Zimmer |
| 7,008,799 | B1 | 3/2006 | Zimmer et al. |
| 7,238,534 | B1 | 7/2007 | Zimmer |
| 2003/0031592 | A1* | 2/2003 | Knappe .................. 422/56 |

FOREIGN PATENT DOCUMENTS

| EP | 0 287 883 A1 | 10/1988 |
| EP | 1 318 397 A1 | 6/2003 |
| GB | 2090659 A | 7/1982 |
| WO | WO 03/095092 A1 | 11/2003 |

OTHER PUBLICATIONS

Data Sheet for Reflotron® HDL cholesterol, Roche Diagnostics Mannheim, Germany, pp. 1-2.
Data Sheet for Reflotron® cholesterol, Roche Diagnostics Mannheim, Germany, pp. 1-2.
Data Sheet for Reflotron® triglycerides, Roche Diagnostics Mannheim, Germany, pp. 1-2.

(Continued)

*Primary Examiner*—Lyle A Alexander
(74) *Attorney, Agent, or Firm*—Dinsmore & Shohl LLP

(57) ABSTRACT

An analytical test element for determining at least one analyte in a liquid is provided comprising a support, at least one detection element, and a channel capable of capillary liquid transport which is at least partially formed by a hydrophilic network, one side of which is at least partially in contact with the inner space of the channel and the opposite side of which is at least partially in contact with the detection element such that liquid can be transported from the channel across the network to the detection element. The invention also concerns the use of the analytical test element to determine an analyte in a liquid and a method for determining at least one analyte in the liquid with the aid of an analytical test element.

25 Claims, 4 Drawing Sheets

OTHER PUBLICATIONS

R. T. Chen; Structural Characterization of Celgard Microporous Membrane Precursors: Melt-Extruded Polyethylene Films; Journal of Applied Polymer Science; 1994; pp. 471-483; vol. 53.

T. Sarada; Three Dimensional Structure of Celgard Microporous Membranes; Journal of Membrane Science; 1983; pp. 97-113.

* cited by examiner

ANALYTICAL TEST ELEMENT

BACKGROUND OF THE INVENTION

The present invention concerns an analytical test element for determining at least one analyte in a liquid, the use of an analytical test element according to the invention to determine an analyte in a liquid and methods for determining at least one analyte in a liquid with the aid of an analytical test element according to the invention.

So-called carrier-bound tests are often used for the qualitative and quantitative analytical determination of components of liquids and especially of body fluids such as blood. In these tests, reagents and, in particular, specific detection reagents and auxiliary reagents, are embedded or immobilized in suitable layers of a solid support. These layers are referred to as detection elements. In order to determine the corresponding analyte the liquid sample is brought into contact with these detection elements. If a target analyte is present, the reaction of liquid sample and reagents usually results in a signal that can be detected optically or electrochemically and, in particular, to a colour change that can be evaluated visually or with the aid of an instrument, usually by reflection photometry. Other detection methods are for example based on electrochemical methods and detect changes in charge, potential or current.

Test elements or test carriers are often in the form of test strips which essentially consist of an elongate support layer of plastic material and detection elements mounted thereon as test fields. However, test carriers are also known that are formed as small quadratic or rectangular plates.

Test elements for clinical diagnostics are often constructed such that the sample application area and the detection area are stacked above one another in a vertical axis. This type of construction is associated with a number of problems. When the test strip loaded with sample has to be inserted in an instrument such as a reflection photometer for measurement, potentially infectious sample material can come into contact with parts of the instrument and may contaminate them. Hence, a spatial separation of the sample application area and detection element is desirable.

A volumetric metering is often very difficult to achieve in these test elements especially in cases in which the test strips are used by untrained persons, for example, for self-monitoring of blood sugar or coagulation. The transport of the liquid sample from the sample application area to the detection element which is necessary for this is often a very critical process with regard to metering the liquid to be analysed and, thus, the reproducibility of the measurement. Such test elements require additional devices such as channels, membranes, papers or fleeces to transport and distribute the liquid samples. This design often means that relatively large sample volumes are required to enable reliable measurements. In the case that for example blood is used as a sample liquid, blood collection is all the more painful for the patient the more blood has to be collected as the sample liquid. Hence, the general goal is to provide test strips which require the smallest possible amount of sample material. Furthermore, the liquid transport should be as rapid as possible to achieve the shortest possible measurement times.

When using fleeces, papers or membranes for liquid transport, the rate of transport is decisively influenced by the properties of the respective material and hence it is not possible to guarantee uniformly high transport rates. Furthermore, major disadvantages of the aforementioned materials are that they have a not inconsiderable intrinsic volume and are themselves capillary active due to their microscopic structure.

Thus, especially fleeces and papers have a large capillary active volume due to their fibre structure which, although enabling the distribution of liquid within the material and transport from the sample application area to the detection element as a result of capillary forces, also results in retention of a not inconsiderable portion of the liquid to be examined. Consequently, a considerable portion of the originally applied sample liquid is not available for the actual detection of the analyte in such test elements so that larger sample volumes have to be used which in turn have the above-mentioned disadvantages for the patient. Furthermore, when several detection elements are arranged behind one another on a common test element the problem occurs that the detection reactions do not start uniformly and simultaneously in the detection elements. Due to the relatively slow liquid transport through capillary active fleeces, papers or membranes, the detection reaction begins considerably sooner in the detection element facing the sample application area than the detection elements that are behind it in the direction of flow. This also applies similarly to the respective detection element itself. In this case the wetting with liquid and thus the start of the detection reaction firstly occurs at the side facing the sample application area so that delays in the start of the detection reaction can also occur within a detection element. Thus non-uniform and non-reproducible reaction time courses and thus erroneous analyte determinations can occur.

In the case of several detection elements arranged one behind the other, carry over of reagents from one detection element into neighbouring detection elements which are behind it in the direction of flow can additionally occur and thus falsify the result of the measurement.

If channel structures are used to transport liquid samples from the sample application area to the detection element, certain minimum and maximum dimensions with regard to width, height and length and surface properties of the channel have to be adhered to in order to enable capillary transport of the liquid. This again puts constraints on the liquid volume to be transported and the transport rate.

Other mechanisms and devices for liquid transport often require the use of active external forces such as pumps thus necessitating additional and hence costly devices.

The channels that have been previously used in test elements often have the disadvantage that they have a not inconsiderable internal volume which, due to capillary activity, retains a portion of the liquid volume to be examined. Thus, also in such test elements a portion of the originally applied sample liquid is not available for the actual analyte detection. As a consequence larger sample volumes have to be used which again has the above-mentioned disadvantages for the patients.

Channels that have previously been used in test elements are usually composed of inert materials that are impermeable to liquids. Although a rapid capillary liquid transport can occur in these channels in the area of the detection element, further structures and devices are necessary to transport the liquid from the capillaries into the detection element.

One method is to integrate the detection element or parts thereof in direct contact with the inner space of the capillary channel such that the detection element is itself a component of the capillary channel. However, this has the disadvantage that sharp changes in the surface properties of the two materials can occur at the sites of transition from the wall of the capillary channel to the detection element which can hinder or completely disrupt the transport of liquid. Hence, it is not possible to guarantee a uniform and simultaneous flow of liquid to be examined to the detection elements. Instead, the wetting and thus the detection reaction occurs earlier in the area of the detection element that faces the capillary space or the sample application area than in sites that are further removed and, hence, it is not possible to achieve a controlled and uniform detection reaction process and a reproducible determination of the analyte.

Test elements in which capillary active materials such as fleeces or similar materials and, in particular, so-called spreading fleeces or fabrics make the junction between the capillary channel and the detection elements, are subject to similar problems and additionally have the aforementioned disadvantages of fleece-like materials for liquid transport.

EP-A-0 287 883 describes a test element that utilizes a capillary interspace between the detection layer and an inert support for volumetric metering. In order to fill the capillary space the test element is dipped in the sample to be examined requiring large sample volumes which is why this type of volumetric metering is more suitable for examining sample material such as urine which is present in excess. In this case, the capillary space is only used for volumetric metering. A spatial separation of the sample application area and site of detection and a directed liquid transport to the site of detection caused by a capillary gap is not provided in the described device. Furthermore, in the described device the detection element itself forms part of the capillary space.

DE 197 53 847 describes a test element for determining an analyte in a liquid which has a channel capable of capillary liquid transport and a detection element on an inert support. The channel capable of capillary liquid transport is characterized according to the invention in that it is at least partially formed by the support and the detection element and extends in the direction of capillary transport from the sample application opening at least to the edge of the detection element that is nearest to the vent hole. A particular disadvantage of this embodiment is that the detection element is a direct component of the channel capable of capillary liquid transport. As a result, the different surface properties of the individual components of the channel can cause the above-mentioned problems such as impairment or interruption of capillary transport or an irregular wetting of the detection element. Furthermore, the liquid to be examined in the channel itself comes into direct contact with the reagents in the detection element and hence in this embodiment there is no spatial separation between the transport space and detection area.

A device for analysing biological fluids is known from DE-A 31 51 291 which comprises a support with a self-filling measuring channel and a laminate arrangement with a filter layer and a reagent material layer. In this test carrier the sample liquid is transported into the test channel by capillary forces and from this channel it enters the laminate located above it where a detection reaction of the target analyte takes place after heating the analytical device. In this device a microporous membrane having pore sizes of less than 1 µm forms the upper cover of the capillary channel as a filter layer. According to the invention this filter membrane has the function of isolating the reagent material layer from interfering components such as cell structures. The main object of this filter membrane is to process the liquid sample before it is analysed in the reagent material layer and change its composition and it is thus already involved in the detection of the analyte. A disadvantage of this is that the very small pore openings of less than 1 µm only allow a very slow penetration of the liquid into the reagent material layer resulting in long measuring times. In particular, when using solutions such as blood which contain particles or cells in high concentrations, the filter membrane can easily become clogged due to the small pore size of the membrane and thus the transport of the liquid to be examined into the detection area can be impaired or interrupted. Consequently, it is not possible in all cases to ensure that the analyte determination can be carried out and is reproducible. Another disadvantage is that the analytical device with the sample contained therein has to be heated in order to determine the analyte. Hence, the use of the analytical device is essentially confined to laboratories.

DE 196 29 657 describes a diagnostic test carrier which contains one or more detection layers on a support layer and a network covering the detection layers which is larger than the detection layers and is attached to the support layer. In order to determine analytes the liquid to be examined is directly applied to the net and flows through it into the detection layers. In this case the sample application area and detection layers are arranged above one another in a vertical axis which results in the aforementioned problems associated with such stack-like arrangements. Before the determination of the analyte there is no specific transport of the liquid to be examined from the sample application area to a distant detection layer in a horizontal direction, for example, by means of capillary channels. Here, the purpose of the network is to transport excess liquid through the network away from the detection layer into the parts of the network extending beyond the detection layer. For this purpose the thickness of the network should be such that the cover on top and the underlying support layer are at such a distance from one another that remaining liquid over the saturated detection layer and in the filled meshes of the network is imbibed by capillary forces into the area under the cover and is led away from the sample application area. In these areas the liquid transport is in a lateral direction due to capillary forces within the network itself or capillary forces between the network and cover or support layer but not capillary forces in which the network forms a wall of a larger capillary gap. Since the network in the described device must fulfil other requirements, it also has different geometric parameters and material properties compared to the network of the present invention.

SUMMARY OF THE INVENTION

It is against the above background that the present invention provides certain unobvious advantages and advancements over the prior art. In particular, the inventor has recognized a need for improvements in analytical test elements for determining at least one analyte in a liquid.

Although the present invention is not limited to specific advantages or functionality, it is noted that the present invention provides a self volume-metering test element that is simple to operate, and which enables a spatial separation of the detection area and sample application area using minimal sample volumes. In addition, liquid transport from the sample application and into the detection area is rapid and complete, such that it imposes no limitations on the time required to analyse a sample. For example, in the case of test elements which have several detection elements, the present invention ensures that the liquid sample reaches the individual detection elements as far as possible at the same time and without carry-over problems and, thus, the individual detection reactions can begin as far as possible at the same time. Furthermore, the simple construction of the test element enables an economical and technically simple manufacture.

In accordance with one embodiment of the present invention, an analytical test element for determining at least one analyte in a liquid is provided comprising a support, at least one detection element, and a channel capable of capillary liquid transport. The channel is at least partially formed by a hydrophilic network, one side of which is at least partially in contact with the inner space of the channel and the opposite side of which is at least partially in contact with the detection element such that liquid can be transported from the channel across the network to the detection element. The analytical test element can be used to determine an analyte in a liquid.

In accordance with another embodiment of the present invention, a method for determining at least one analyte in a liquid is provided comprising a) contacting a liquid sample with an analytical test element, the test element comprising a support, at least one detection element, and a channel capable of capillary liquid transport, wherein the channel is at least partially formed by a hydrophilic network, one side of which is at least partially in contact with the inner space of the channel and the opposite side of which is at least partially in contact with the detection element such that liquid can be transported from the channel across the network to the detection element; b) transporting the liquid sample in the channel by capillary forces at least as far as the area of the detection element; c) transporting the liquid sample from the channel across the network to the detection element; d) reacting the liquid sample with at least one reagent in the detection element; and e) observing an indicator of the presence, absence, or concentration of the analyte.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1A:
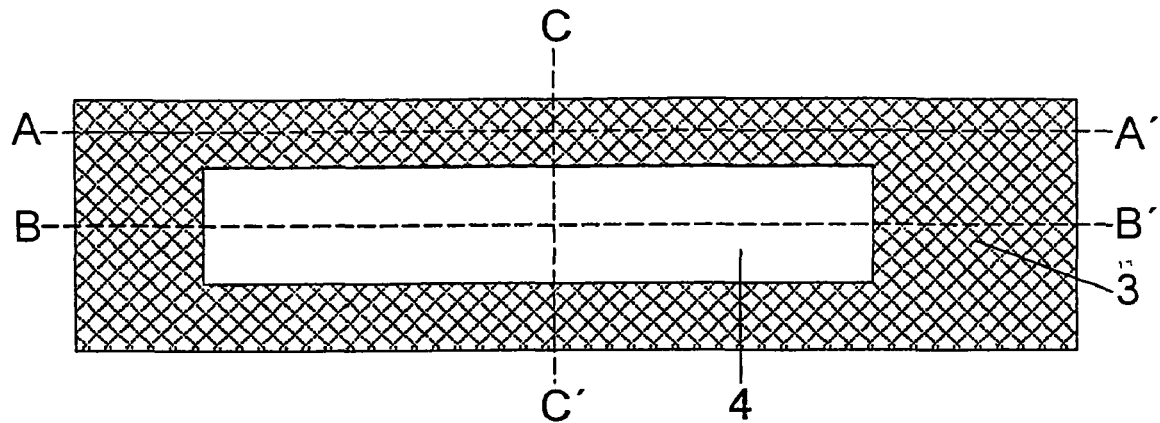
FIG. 1A shows a schematic top-view of a test element in accordance with the principals of one particular embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

In accordance with one embodiment of the present invention, an analytical test element for determining at least one analyte in a liquid is provided comprising a support, at least one detection element, and a channel capable of capillary liquid transport. The channel is at least partially bordered or formed by a hydrophilic network. According to the instant embodiment, one or more detection elements are in direct contact with the side of the network that faces away from the capillary gap. Hence, at least some partial areas of the network are located between the capillary gap and the detection element. The network represents a boundary surface of the capillary gap and enables the liquid sample to be transported from the sample application area through the capillary gap to the areas of the capillary gap which are located below the detection element but separated by the network. The surface properties and geometric dimensions of the network and of the capillary channel can affect the way in which the test element functions according to the invention. Thus, for example, in one embodiment the liquid sample is transported within a few seconds from the sample application area through the capillary gap to the opposite vent hole without liquid initially leaving the capillary gap beyond the network. In this embodiment a blood drop of about 30 µl volume can for example fill the entire capillary gap which has a width of about 2 mm, a height of about 200 µm, and a length of about 25 mm within about 3 to about 5 seconds. This enables the flow of liquid sample to very rapidly and substantially simultaneously reach the detection elements.

Under normal conditions such as atmospheric pressure the liquid can only pass according to the invention through the network and flow into the respective detection elements at sites at which one or more detection elements are located on the other side of the network. Accordingly, a direct contact of the detection elements with the side of the network that faces away from the capillary gap is typically made.

The capillary gap is rapidly filled and the detection elements are subsequently wetted substantially uniformly and simultaneously when the network, the capillary gap, and the detection element have suitable surface properties and geometric dimensions, and the individual elements are arranged suitably relative to one another. This increases the precision and reproducibility of the analyte determination.

The geometric dimensions and the volume of the channel or capillary gap capable of capillary liquid transport can be adapted to the sample volumes to be examined. For the typical case that the channel has an essentially rectangular cross-section, one dimension, for example the height of the channel, is determined by the physical limits of capillary activity. The volume of the capillary channel can then be adjusted by suitable selection of the two other dimensions such as length and width. In the case of aqueous liquids the height of the capillaries is of the order of magnitude of between about 10 and about 500 µm, typically between about 20 and about 300 µm, and more typically between about 50 and about 200 µm. Depending on the desired volume, the width can then be several mm, typically about 1 to about 5 mm, more typically about 1 to about 3 mm, and the length can be up to a few cm, typically about 0.5 to about 5 cm, more typically about 1 to about 3 cm. However, the capillary properties of a channel can not only depend on the geometric dimensions but also on other parameters such as surface properties and hydrophobicity of the channel walls or the rheological properties of the sample liquid. The said dimensions are not to be regarded as limitations but rather as examples. The optimal dimensions and surface properties of the capillary gap can be determined by a person skilled in the art such that the properties of the channel can be adapted to the respective requirements.

The capillary gap largely consists of a support substance which is designed such that it can form a capillary channel typically at the sites where it is covered with the network. In one particular embodiment, a corresponding recess is made in the support substance for this purpose, e.g., embossed, etched or milled. In another embodiment, the geometry of the capillary channel is not primarily determined by the shape of the support substance but mainly by additional intermediate layers. In this case one or more spacers are typically attached to a support in such a manner that the sides that face the future capillary channel are at a distance from one another that corresponds to the width of the future capillary gap. In this case the height of the future capillary gap is determined by the height of the spacers. The length of the future capillary gap can be determined by the length of the spacers.

The intermediate layer can be made of a double-sided adhesive tape which in addition to determining the geometry of the capillary channel can also be used to join the other components, i.e., support and network, involved in the formation of the capillary-active zone.

In yet another embodiment of the present invention, the shape of the future capillary channel is given by the design for the intermediate layer or of the spacers. Thus, by punching or cutting the spacer material it is for example possible to design certain areas such that they serve as sample application areas or vent holes.

In still another embodiment, two double-sided adhesive tapes are attached as an intermediate layer and spacer to a support at a distance from one another which corresponds to the width of the capillary channel. A capillary channel can then be formed by mounting the network on the double-sided adhesive tapes.

Inert materials that do not absorb the liquids to be examined are typically used for the walls of the capillary gap and for the support material and eventual intermediate layers. These materials can include non-absorbent materials of which plastic foils such as, for example, polystyrene, polyvinyl chloride, polyester, polycarbonate or polyamide are typical. Metal foils, ceramics or glass are suitable as additional support materials. However, it is also possible to impregnate absorbent materials such as wood, paper or cardboard with water repellent agents.

The ends of the capillary gap can be bordered by a sample application opening and a vent opening. The sample application opening is typically designed such that it ensures that sample liquid enters the capillary channel. This can, for example, be achieved by the fact that the sample drop can be directly contacted with one of the surfaces that forms one of the inner surfaces of the capillary such as, for example, by contacting the sample drop with the corresponding end of the capillary gap. However, the sample application opening can also be formed by a cut-out in at least one of the walls forming the capillary gap. Suitable selection of the geometry and dimensions of the cut-out ensures that the liquid drop comes into contact with the capillary-active zone with very high probability independently of the exact position of the application and is readily sucked into the interior of the capillary. For example, the size of the exposed surface can be selected such that at least one site on the liquid drop applied thereto comes into contact with the capillary-active zone. For example, one dimension of the cut-out, i.e., its width, can be selected such that the diameter of the liquid drop is slightly larger than the selected dimension of the cut-out. In the case of the drop of about 3 µl, a width of the cut-out of about 1 mm is suitable, and correspondingly larger cut-outs are suitable for larger amounts of liquid. The sample drop is typically sucked into the capillary channel by means of the fact that the surface exposed by the cut-out is hydrophilized and directly merges into the capillary-active zone at least in the direction of the capillary transport channel. A typical method of generating such a sample application opening or vent opening is to use intermediate layers that are punched or cut to size, for example double-sided adhesive tapes, in the aforementioned manner. Such an embodiment is described, for example, in WO 03/095092, the disclosure of which is hereby incorporated by reference. Other typical sample application openings can be designed such that they can be brought into direct contact with a drop of sample liquid and this drop can then be transported to the detection elements by capillary forces. Such an embodiment is described, for example, in DE 197 53 850 A1, the disclosure of which is hereby incorporated by reference.

A capillary's ability to suck up a liquid depends on the ability to wet the channel surface with liquid. In the case of aqueous samples this means that a capillary must be made of a material whose surface tension is near to or exceeds the surface tension of water which is 72 mN/m. In this connection hydrophilic surfaces are water-attracting surfaces. Aqueous samples, also including blood, spread well on such surfaces. Such surfaces are characterized among others in that at the interface a water drop forms an acute rim or contact angle on it. In contrast, an obtuse rim angle is formed at the interface between the water drop and surface on hydrophobic, i.e., water repellent surfaces.

Sufficiently hydrophilic materials for constructing a capillary which rapidly sucks up aqueous samples are, for example, glass, metal or ceramic. However, the suitability of these materials is limited in the case of applications in test carriers since they have some disadvantages such as risk of breakage in the case of glass or ceramics, or change in the surface properties over time in the case of numerous metals. Hence, plastic foils or moulded parts are typically used to manufacture test elements. The plastics that are used usually hardly exceed a surface tension of 45 mN/m. Even with the most hydrophilic of the conventional plastics such as, for example, polymethylmethacrylate or polyamide, it is only possible to construct capillaries that suck very slowly, if at all. Capillaries made of hydrophobic plastics such as polystyrene, polypropylene or polyethylene essentially do not suck aqueous samples. Thus, plastics have to be made hydrophilic, i.e., hydrophilized for use as a construction material for test elements with capillary-active channels.

In accordance with still yet another embodiment of the present invention, the analytical test element can further comprise at least one, but more typically two, and even more typically two opposing sides, of the inner surface of the channel capable of capillary liquid transport are hydrophilized. For example, the hydrophilic network can form such a hydrophilic inner surface of the capillary gap.

If more than one surface is hydrophilized, then the surfaces can be made hydrophilic either by the same or different methods.

The hydrophilization is typically employed when the materials which form the capillary-active channel, in particular the support, are themselves hydrophobic or only very slightly hydrophilic, for example because they consist of unpolar plastics. Unpolar plastics such as polystyrene, polyethylene, polyethylene terephthalate or polyvinyl chloride are typical as support materials because they do not absorb the liquid to be examined and, thus, the sample volume can be effectively utilized for the analyte determination. The hydrophilization of the surface of the capillary channel has the effect that an aqueous sample liquid readily enters the capillary channel and is rapidly transported there to the detection element.

Typically, the surface of the capillary channel is hydrophilized by using a hydrophilic material for its manufacture which itself is not or not significantly able to absorb the sample liquid. Alternatively, the hydrophobic or only very slightly hydrophilic surface can be hydrophilized by a suitable coating with a stable hydrophilic layer that is inert towards the sample material, for example by covalently binding photo-reactive, hydrophilic polymers on a plastic surface, by applying layers containing wetting agents or by coating surfaces with nanocomposites by means of sol-gel technology. Hydrophobic carriers can also be hydrophilized by applying complete hydrophilic surfaces, for example, in the form of foils. Moreover, it is possible to increase the hydrophilicity by thermal, physical or chemical treatment of the surface, for example, by treating the surface with wetting agents such as dioctyl sodium sulfosuccinate, oleoyl sarcosine acid, or combinations thereof.

The network of the diagnostic test carrier according to the present invention may itself not be capillary-active or absorbent so that the sample liquid is available as entirely as possible for the detection element. Networks have proven to be particularly suitable which, when immersed vertically in water, enable water to rise to a height of less than 2 mm. Monofilament hydrophilic fabrics are typically used as the network. Either the fabric material can itself be hydrophilic or it can be made hydrophilic, for example, by treatment with wetting agents.

The mesh width of the network can affect function of the test element according to the present invention.

The mesh width of the network is typically within certain limits. On the one hand, the distance between the individual components of the network should not be too large so that the liquid can be transported laterally within the capillary gap without liquid escaping from the network or a disruption of the capillary transport occurring. On the other hand, the distance between the individual components of the network should not be too small in order that the liquid can be rapidly conveyed to the detection elements by means of capillary forces resulting from the capillary-active interaction of the network and the detection elements that are in direct contact with the network or a capillary activity of the detection element itself. The network itself is not capillary active so that liquid is not transported through the network at the sites of the network that are not in contact with the detection elements. Liquid can only be transported through the network itself when a capillary-active element, in particular, a capillary-active detection element, is in direct contact with the network on the side of the network facing away from the capillary gap. As a result of this contact between the capillary-active detection element and the network which is itself not capillary-active, additional capillary-active spaces are formed in the contact zone of these two elements which then enable the liquid to be transported from the space of the capillary gap across the network into the detection element.

The thickness of the network can be in a range in which the detection element lying on top is at a certain distance from the inner space of the capillary gap such that continuous capillary-active spaces can form in the contact zone between the capillary channel, network and detection element. In particular, such capillary-active spaces can exist between the interspaces of the network and the underside of the detection element. As a result, the liquid sample can be sucked by capillary forces into the detection element across the meshes of the network that are wetted with liquid.

Networks with a mesh width between about 10 and about 500 µm, typically between about 20 and about 300 µm, more typically between about 50 and about 150 µm, a fibre or wire diameter between about 10 and about 300 µm, typically between about 30 and about 150 µm, more typically between about 50 and about 100 µm, and a thickness between about 10 and about 500 µm, typically between about 20 and about 300 µm, more typically between about 50 and about 150 µm are particularly suitable for this. The network typically consists of a hydrophilic fabric. It has surprisingly turned out that non-hydrophilic, inexpensive fabric that can in return be readily processed can also be used when the surface of the fabric is hydrophilized. Polyethylene terephthalate is used as a typical net material and the network made of this material is subsequently treated and, thus, hydrophilized with a wetting agent such as dioctyl sodium sulfosuccinate or oleoyl sarcosine acid.

The term network in the sense of the present invention is, however, not limited to monofilament fabrics. In principle, all materials can be used as a network in the sense of the present invention which as a result of their macroscopic or microscopic structure enable them, on the one hand, to act as a component of a capillary gap such that liquid does not escape from the material while liquid is transported in the capillary gap and, on the other hand, are able to form continuous capillary spaces by direct contact with a detection element through which the liquid sample can be passed from the capillary gap through the material into the detection element. Materials are typically suitable which have void spaces with a diameter between about 10 and about 500 µm, typically between about 20 and about 300 µm, and more typically between about 50 and about 150 µm. Such materials can be, for example, polyfilament fabrics, knitted fabrics or sieve or pore structures in addition to monofilament tissues.

The network does not necessarily have to form an entire side face of a capillary gap in order to enable the test element to function according to the invention. In accordance with yet still another typical embodiment, the network can form only one part of the walls of the capillary gap. However, in these cases the network must be at least partially in direct contact with the inner space of the capillary gap and at least partially in direct contact with the detection elements so that liquid can be transported from the inner space of the capillary gap into the detection element. Such embodiments are more typical when the network itself is expensive. In this case such embodiments in which the network is only involved in the construction of the capillary gap in the areas of the detection elements can considerably reduce the manufacturing costs.

The use according to the invention of a capillary-active channel with a network as a boundary has the following advantages.

Since the channel capable of capillary liquid transport fills with the liquid to be examined in a very short time and this liquid can pass into the adjoining detection elements across the network essentially uniformly and simultaneously, this ensures that inhomogeneous wetting of the detection element with the liquid sample and, thus, a falsification of the measurement is avoided;

A substantially uniform and simultaneous detection reaction can be achieved; and Furthermore, the liquid volume in the capillary channel can be exactly and reproducibly determined by the geometric dimensions of the capillary channel. The capillary gap according to the invention thus also fulfils volumetric metering functions of the sample liquid. The precision and reproducibility of the measurement is thus increased.

In the case of test elements in which the time course or the result of a detection reaction in the detection element is detected in a spatially exactly defined area, for example, in the case of optical detection in a special instrument and it is thus desirable to separate the sample application area and detection zone, for example, for reasons of instrument hygiene, use of a capillary-active channel has the additional advantage that the liquid sample is transported very rapidly from the sample application opening in the test element to the detection site in the detection element. Hence, this does not impose any time limitations on the analysis of the sample. Furthermore, such an arrangement can be used more comfortably by the user.

In addition to the already mentioned advantages, the test element according to the invention has further advantages. The spatial separation of the sample application area and signal detection together with the volumetric metering of the sample enables the sample material to be handled hygienically. In the case of optical detection, for example, by means of a reflection photometer, this largely eliminates contamination of the instrument since the sample can, for example, be applied to a test element which protrudes from the instrument, the amount of sample required to determine the analyte is sucked into the capillary channel and is transported automatically and in a metered manner without further measures to the detection zone of the test element located in the interior of the instrument.

Furthermore, the test element according to the present invention requires significantly less sample material than conventional test elements. This is achieved by optimizing the sample flow exactly at the site of determination and by the non-absorbent and non-self-capillary-active properties of the network which have the effect that almost the entire amount of liquid to be examined that is applied is available for the actual detection reaction. In the case that the sample is blood, this can simplify sample collection for the person to be examined and is above all associated with less pain.

A detection element contains the reagents necessary for the detection reaction of the target analyte in the sample and optionally auxiliary substances. The detection element can also contain only some of the reagents or auxiliary substances. Such reagents and auxiliary substances are well known to a person familiar with the technology of analytical test elements or diagnostic test carriers. For example, enzymes, enzyme substrates, indicators, buffer salts, inert fillers and such like can be contained in the detection elements for analytes that can be enzymatically detected. The detection analyte can be composed of one or more layers and additionally contain a cover typically on the side of the detection element which is not contacted with the sample. For the more typical case that the detection reaction leads to an observable change in colour, which in this connection should be understood as either a change in colour, the formation of a colour, or the disappearance of colour, the support should allow for a visual or optical observation of the detection reaction by suitable measures. For this purpose the support material and the network or a possible cover of the detection element can themselves be transparent or the support material and the network or a possible cover of the detection element can have a transparent cut-out on the detection side. If the detection element is not surrounded by a cover, the change in colour of the detection element can also be determined directly typically by means of a reflection photometric determination.

In addition to detection reactions which result in colour changes, other detection methods are also known to a person skilled in the art which can be achieved with the described test element, for example, electrochemical sensors or chemical, biochemical, molecular-biological, immunological, physical, fluorimetric or spectroscopic detection methods.

The detection element is typically comprised of materials that are able to take up the liquid to be examined with the analyte contained therein. These materials can be, in particular, absorbent materials such as fleeces, fabrics, knitted fabrics, papers or porous plastic materials. Suitable materials must be able to carry reagents that enable the detection of the analyte to be determined. Typical materials for the detection element are papers or porous plastic materials such as membranes. More typical porous membrane materials are polyamide, polyvinylidene fluoride, polyether sulfone and polysulfone membranes. The reagents for determining the analyte to be detected can typically be incorporated by impregnating them in the aforementioned materials.

So-called open films are typically suitable for the detection element such as those described in EP-B-0 016 387, the disclosure of which is hereby incorporated by reference. In this case an aqueous dispersion of film-forming organic plastic solids is added as fine, insoluble, organic or inorganic particles and the reagents required for the detection reaction are additionally added. Suitable film formers are typically organic plastics such as polyvinyl esters, polyvinyl acetates, esters of polyacrylic acid, polymethacrylic acid, polyacrylamides, polyamides, polystyrene, mixed polymers, for example, of butadiene and styrene, or of maleic acid ester and vinyl acetate, or other film-forming, natural and synthetic organic polymers and mixtures thereof in the form of aqueous dispersions. Although the reagents required for the detection reaction are normally added to the dispersion used to prepare the open films, it may also be advantageous to impregnate the formed film with reagents after its production. It is also possible to pre-impregnate the fillers with the reagents. A person skilled in the art knows potential reagents that can be used to determine a certain analyte.

The detection element can also be provided with components which allow interfering sample components to be excluded from the detection reaction and thus act as filters, for example, for particulate sample components such as blood cells. For example, the red blood pigment haemoglobin which is contained in the erythrocytes interferes with the analysis of blood samples in the case of visual or optical detection methods. It is expedient to remove these interfering components before the actual detection reaction of the sample, for example, whole blood. This can be achieved by sample preparation before applying the sample to the test element, for example, by centrifuging whole blood and subsequently isolating serum or plasma. It is more convenient and also more simple for the user when the test element itself carries out this separation step by a suitable construction. A person skilled in the art knows means from test strip technology which ensure a reliable exclusion of erythrocytes and other interfering blood components. For example, it is possible to use semipermeable membranes or glass fibre fleeces as, for example, those known from EP-B-0 045 476 to separate red blood corpuscles, the disclosure of which is hereby incorporated by reference.

The detection element can be contacted with the network in a manner known to a person skilled in the art. It has proven to be more typical to firstly place the detection elements on the network and then glue at least two lateral, typically opposite, edge areas of the detection element to the network. It is more typically attached at least on the sides that are perpendicular to the course of the capillary gap. In this manner the detection element can be immobilized and directly contacted with the network without contaminating the contact surface itself with adhesives. In another typical embodiment this gluing is achieved by hot-melt adhesive. Other contacting and attachment methods such as welding can be employed in accordance with the present invention, which methods are known to a person skilled in the art.

The dimensions of the detection element do not necessarily have to match the dimensions of the capillary channel or the network. The detection element can contain areas which, although being connected to the network, are not in fluidic connection with the capillary gap. Such areas are, for example, areas of the detection element which are located over side boundaries of the capillary gap. In such cases it has proven to be expedient to use detection elements which themselves ensure that the liquid is further distributed over the entire volume of the detection element. Such detection elements can, for example, have fleece structures which further distribute the liquid sample within the detection element. In these cases the transport of liquid through the network serves above all to make a liquid contact between the inner space of the capillary gap and the detection element and, thus, ensure a flow of liquid into the detection element whereas the distribution of liquid within the detection element is then by means of special structures of the detection element itself. Such arrangements can have applications when test elements are manufactured on an industrial scale since the use of network structures and detection elements of the same width can considerably simplify the production process.

The test element according to the invention can be suitable for determining several parameters on a single test element. For this purpose the test element contains not only one detection element but rather several detection elements which can typically detect different analytes. However, in order to increase the sensitivity or specificity of the analyte determination or extend the detectable concentration range, there may also be several detection elements on the test element which detect the same analyte. In this case identical or different detection reactions can be used.

If a test element is designed as a multiparameter test strip, the detection elements are typically arranged behind one another in the direction of liquid flow.

As already mentioned in the case of test elements which use fleeces or similar materials to transport or distribute the sample liquid, the liquid transport in these materials is relatively slow so that the flow of sample liquid to the individual test elements is considerably retarded and, thus, there are delays in the start of the detection reaction in the individual detection elements. This in turn considerably reduces the reproducibility of the detection. The slow transport of liquid past several detection elements can also result in carry-over or depletion artefacts and, thus, to inaccurate analyte determinations. Furthermore, in such test elements dosing problems often occur since a large portion of the liquid sample remains bound in the fleece itself. If too little sample liquid is applied, the rear detection elements may no longer receive sufficient sample liquid for an exact analyte determination. If, in contrast, too much sample liquid is applied, an overdosage of the sample can occur especially in the first test elements. In addition, the aforementioned disadvantages to the patient of large sample amounts occur.

The use of a network according to the invention which borders a capillary gap can eliminate these problems of prior multiparameter test elements.

As the result of the capillary gap according to the invention the liquid volume is transported and distributed over the entire length of the capillary gap within a very short time such that the flow of liquid sample to each individual detection element is substantially simultaneous. Hence, the detection reaction begins essentially simultaneously and in an exactly defined manner thus increasing the reproducibility and measurement accuracy. In addition, carry-over problems are avoided. Furthermore, the network is itself not capillary-active so that liquid can only be transported from the capillary gap in the areas of the detection elements. This and the fact that the network itself does not have an intrinsic capillary-active volume considerably reduces the required amount of sample which reduces the negative effects on the patient.

In accordance with another embodiment of the present invention, several detection elements can be arranged one behind the other on the network and each can be separated by areas that are used to attach and/or separate the individual detection elements. These attachment and separation areas typically have liquid-repellent and, in particular, hydrophobic properties and directly adjoin the respective detection elements. As a result, they restrict the transport of liquid such that liquid can only be transported from the capillary gap through the network into the detection elements without liquid being able to reach the spaces between the individual detection elements. This can again considerably reduce carry-over problems and the required sample volume.

The use of hot-melt adhesive to attach the individual detection elements can also be used to separate the individual detection elements from one another. For this, the individual detection elements are firstly mounted on the network. In a subsequent step the individual detection elements are attached with hot-melt adhesive typically on the sides of the detection elements that are perpendicular to the capillary gap in a manner known to a person skilled in the art such that the hot-melt adhesive is applied in a liquid form to the edges of the respective detection element and flows into the network underneath and cools down. As a result, the detection elements are themselves immobilized in direct contact with the network and, on the other hand, separated from one another by the hydrophobic hot-melt adhesive in the spaces between them. The properties and processing conditions of the hot-melt adhesive such as viscosity, melting temperature and cooling rate can be selected by a person skilled in the art in such a manner that the hot-melt adhesive flows into the network and attaches the detection elements to it and separates them from one another, but does not flow through the network into the capillary gap itself which would have a major effect on the transport of liquid within the capillary gap or may even prevent transport.

Such a multiparameter test element can be more typically used to detect analytes in a diagnostic context. Thus, for example, several different analytes whose concentrations or absence or presence is each known to be changed in a characteristic manner when a certain clinical picture is present, can be determined on a common test element. The simultaneous measurement of several such associated parameters enables the simultaneous determination of different analytes in a single operation which enables a rapid diagnosis. Furthermore, by taking into consideration specific combinations of the individual analytical results, diagnoses can often be made which would be impossible if only one parameter were observed. In particular, the specificity and/or sensitivity of the diagnostic method can thus be increased. Such multi-parameter test elements can, for example, be designed as a lipid panel with detection elements for total cholesterol, HDL cholesterol, LDL cholesterol and/or triglycerides. Other possible multiparameter test elements can, for example, include the afore-mentioned lipid parameters and other parameters such as glucose. Test elements are also possible for the simultaneous determination of glucose and glycosylated haemoglobin and/or total haemoglobin.

A multiparameter test element according to the invention can be used to determine parameters which are associated with an increased risk or presence of cardiovascular diseases. Such parameters are, for example, total cholesterol, HDL cholesterol, LDL cholesterol and triglycerides. In this case the respective detection elements can be immobilized behind one another on the network in the aforementioned manner. A combination of detection elements for cholesterol, HDL cholesterol and triglycerides on one test element is more typical. The detection elements for this can be produced in a manner known to a person skilled in the art. In the present case they can be based on detection methods that are used for reflectometric analyte determinations. Such detection methods are, for example, described in the data sheets for Reflotron® HDL Cholesterol, Reflotron® Cholesterol, and Reflotron® Triglycerides (all from Roche Diagnostics, Mannheim, Germany).

The aforementioned aspects of the invention can either be used alone or in any combination.

Figure 1B:
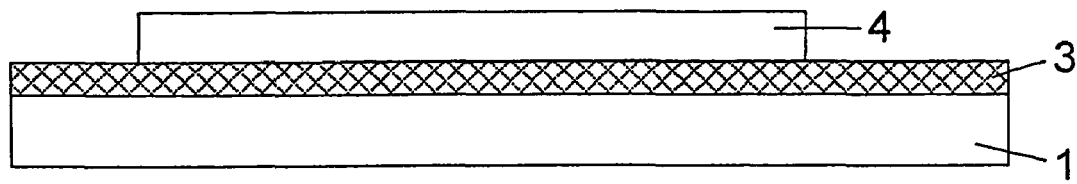
FIGS. 1B to 1D each show cross-sections along the lines A-A', B-B' and C-C' of FIG. 1A, respectively.
Figure 1C:
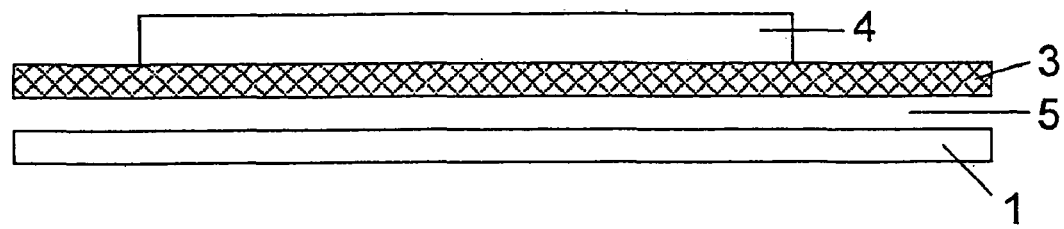
Figure 1D:
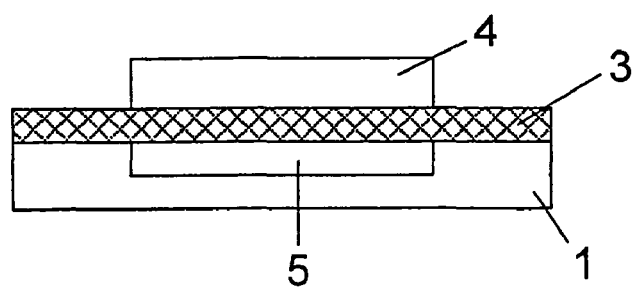
Figure 2A:
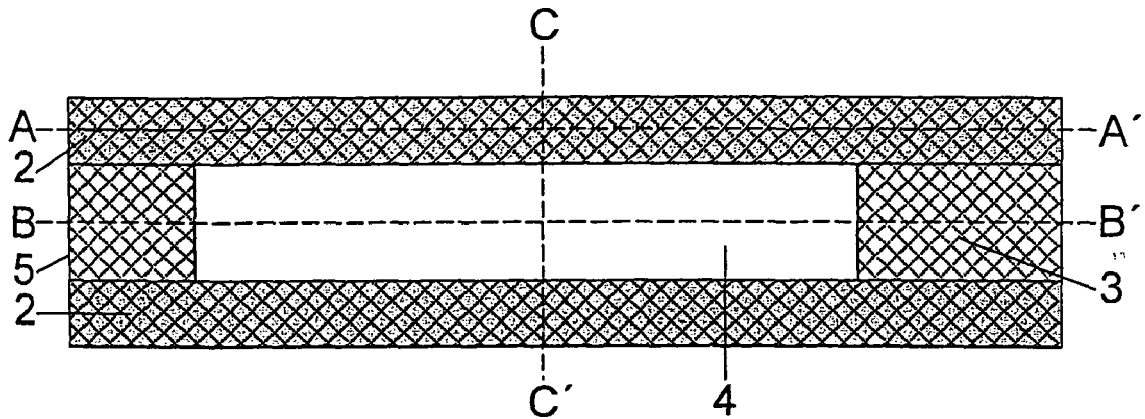
FIG. 2A shows a schematic top-view of a test element in accordance with the principals of one particular embodiment of the present invention.
Figure 2B:
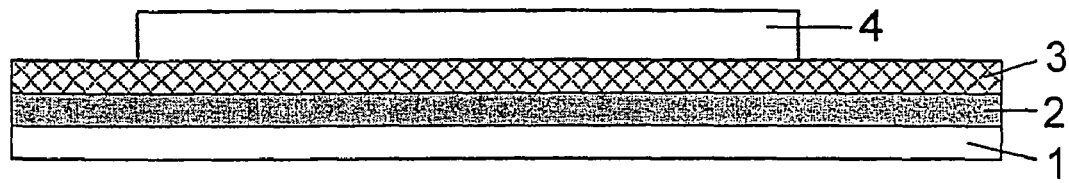
FIGS. 2B to 2D each show cross-sections along the lines A-A', B-B' and C-C' of FIG. 2A, respectively.
Figure 2C:
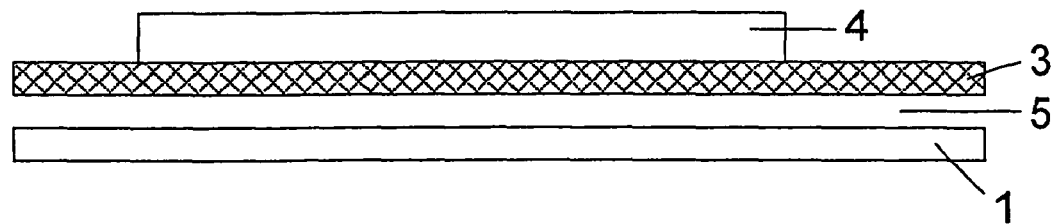
Figure 2D:
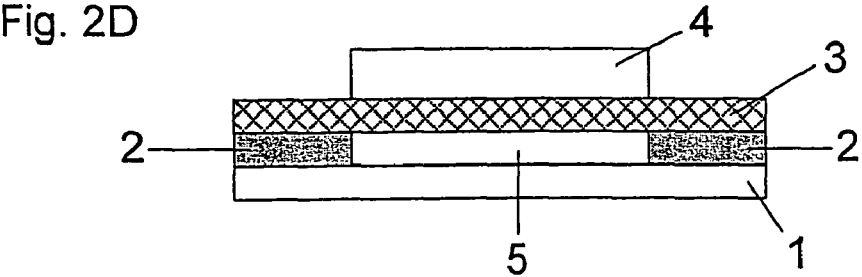
Figure 3A:
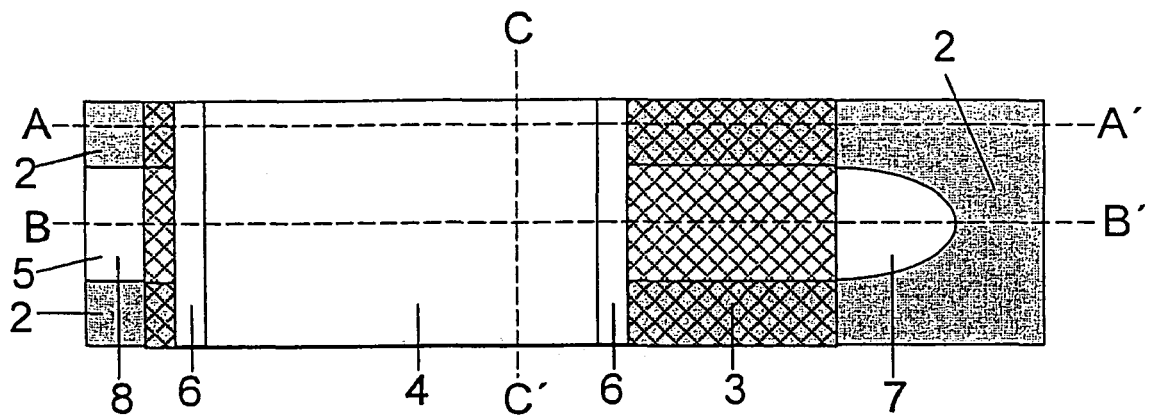
FIG. 3A shows a schematic top-view of a test element in accordance with the principals of one particular embodiment of the present invention comprising a sample application area and vent hole.
Figure 3B:
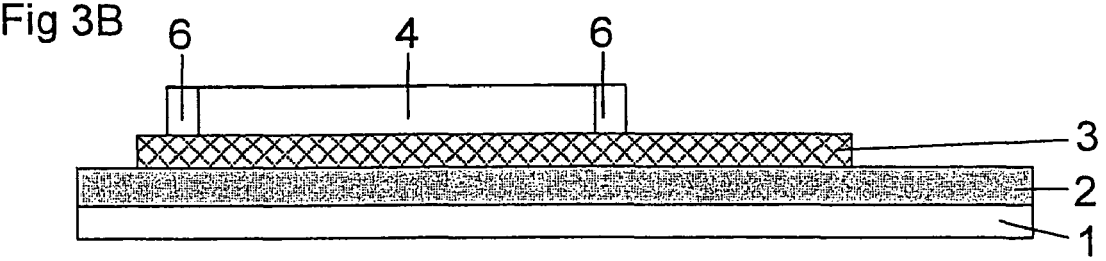
FIGS. 3B to 3D each show cross-sections along the lines A-A', B-B' and C-C' of FIG. 3A, respectively.
Figure 3C:
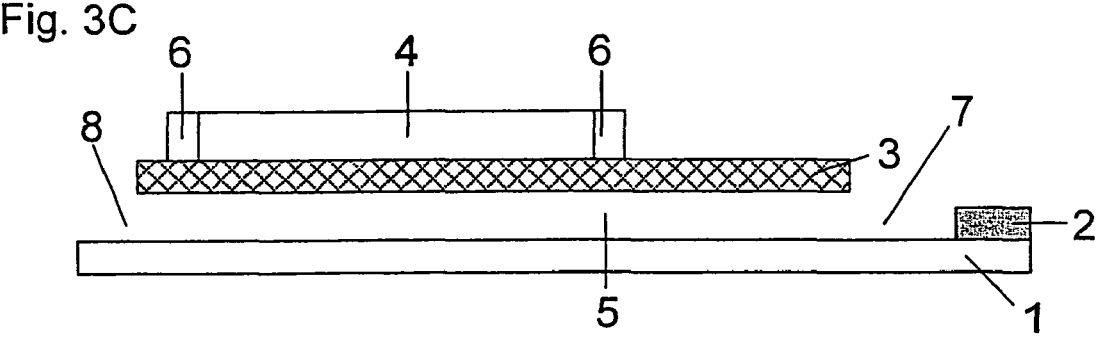
Figure 3D:
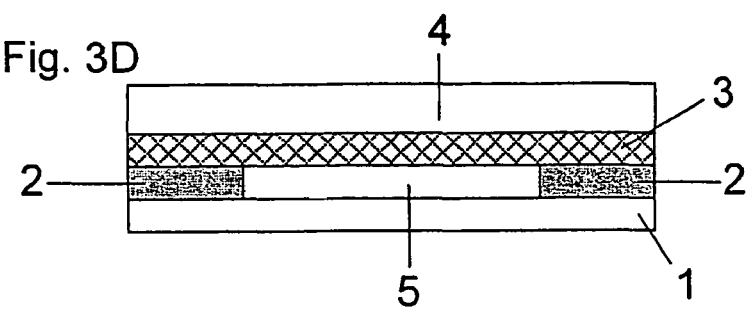
Figure 4A:
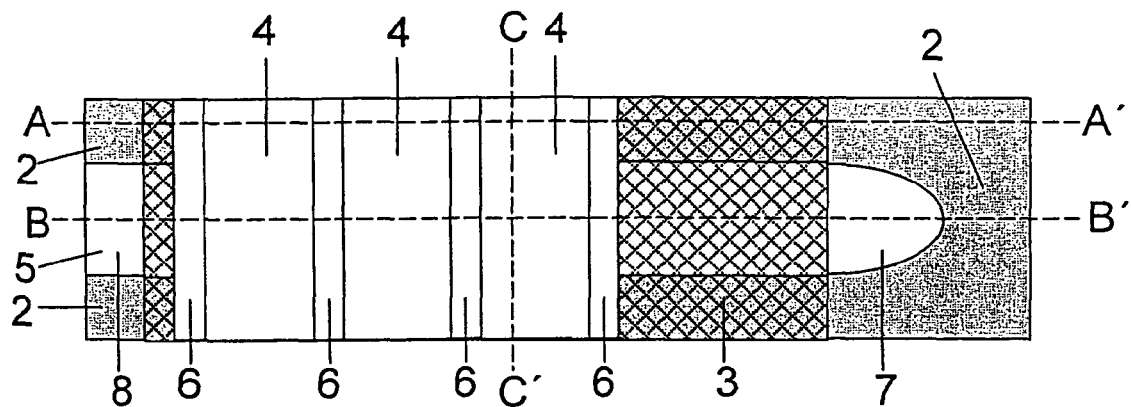
FIG. 4A shows a schematic top-view of a test element in accordance with the principals of one particular embodiment of the present invention comprising several detection elements behind one another and a sample application area and vent hole.
Figure 4B:
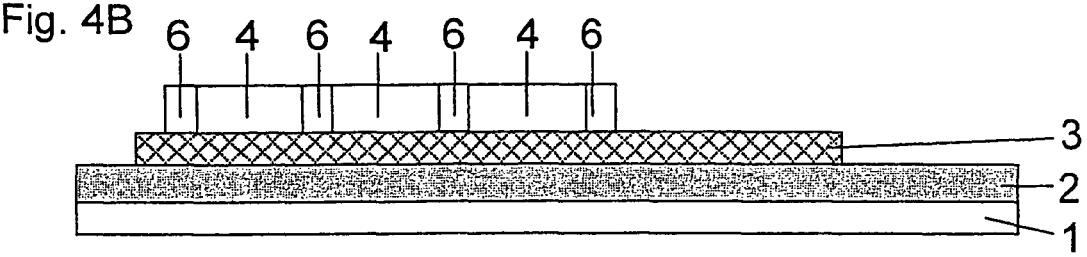
FIGS. 4B to 4D each show cross-sections along the lines A-A', B-B' and C-C' of FIG. 4A, respectively.
Figure 4C:
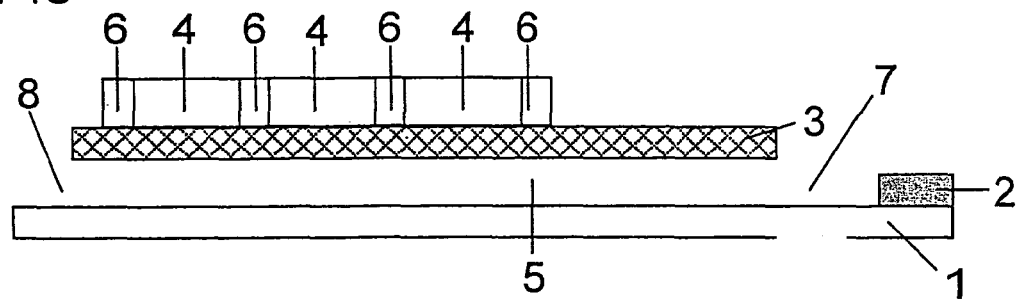
Figure 4D:
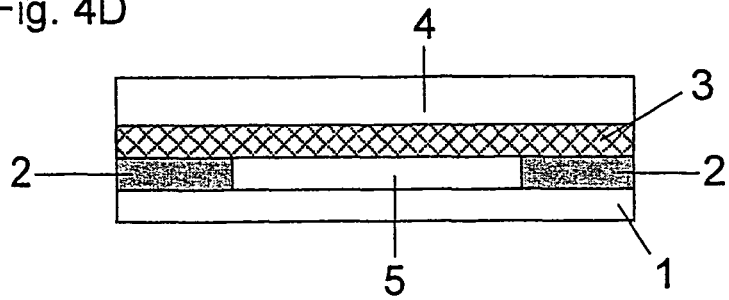

FIG. 1 shows schematically various views of a typical embodiment of the test element according to the invention (FIGS. 1A to 1D). The combination of the views provides a three-dimensional impression of the test element according to the invention. FIG. 1A shows a top-view of the test element in which the support (1) is not visible since it is completely covered in this embodiment by the network (3) and the detection element (4). The test element consists of a support (1) which is designed such that in the area where it is covered by the network (3) it forms a capillary gap or channel (5) together with the network (3). A depression can, for example, be embossed, etched or milled into the support (1). In the embodiment shown, the support (1) has a U-shape as shown in FIG. 1D in the cross-section along the line C-C'.

FIGS. 1B to 1C show longitudinal sections through the test element which run along the lines A-A', B-B' and C-C'. FIG. 1B shows a longitudinal section in the area of the lateral walls of the capillary channel (5), FIG. 1C shows a longitudinal section in the area of the capillary channel (5).

The network (3) is typically attached to the support (1) by gluing, but can also be attached by other techniques known to a person skilled in the art such as, for example, welding. In the embodiment shown, the network (3) is applied over the entire basal surface of the support (1) in such a manner that it forms a capillary channel (5) together with the support (1) which enables a liquid drop to be directly contacted with the capillary channel (5) for sample application. Due to the open construction of the channel (5), a vent hole is located on the side of the capillary channel (5) opposite to this sample application side which allows air to escape when the channel (5) is filled with liquid by capillary forces and, thus, enables a complete and uniform filling of the capillary channel (5). In addition, embodiments of the test element are possible in which the venting occurs through the network (3) and, thus, a vent hole is not necessary. In this case, the network (3) is typically connected with the other components of the test element in such a manner that it ensures venting behind the detection element (4), or in the case of a multiparameter test element, behind the last detection element in order to ensure an optimal filling. The capillary channel (5) extends from the sample application site over the area which is below the detection element (4) up to the vent hole at the opposite end and, thus, ensures a homogeneous sample distribution typically in the area which is below the detection element (4).

The detection element (4) is in direct contact with the network (3). The detection element (4) can be attached to the network (3) by techniques known to a person skilled in the art. However, care should be taken that the liquid sample can be transported from the network (3) into the detection element (4). In the present example, the detection element (4) has a width which corresponds to the width of the capillary gap (5) and a length which is shorter than the length of the capillary gap (5). In other embodiments, dimensions of the detection element (4) are also possible which deviate therefrom. For example, the length and/or the width of the detection element (4) can be less than that of the corresponding dimensions of the capillary gap (5) especially in cases in which it does not make sense to produce detection elements with large areas for financial or constructional reasons. On the other hand, the length and/or width of the detection element (4) can be larger than the corresponding dimensions of the capillary gap (5) especially in cases in which it is economic to produce detection elements with large areas and where the corresponding production processes for the test elements have been optimized for detection elements that have the same width as the network or the support (1). This is typically the case for test strips which are not subdivided into their final form until after the individual components have been assembled, for example, by cutting or punching flat intermediate products. In these cases, the detection elements (4) typically have special properties or structures, for example, fleece structures which allow the uniform distribution of the liquid sample in the detection element.

The test element is used by contacting the sample application site with the sample liquid, for example, with a blood drop on the finger tip. In doing so the sample liquid comes into contact with the capillary channel (5) which is filled with sample liquid by capillary forces until it is filled at least up to the area of the detection elements (4). This occurs in a very short time, typically in a few seconds, due to the inventive design of the test element. Afterwards, contact of the test element with the remaining sample liquid can be interrupted, for example, by removing the test element from the patient's finger since the inventive operating mode of the test element ensures that the required amount of sample to determine the analyte is present in the test element in a very short time. After the capillary channel (5) has been filled, the liquid sample is transported through the network (3) into the detection element (4) as a result of the inventive properties of the network (3) and the capillary interspaces commonly generated by the spatial arrangement of the network (3) and detection element (4). There the detection reaction occurs by means of which the presence or absence or the concentration of the analyte to be determined can be ascertained. Detection reaction and detection methods that can be used to detect a certain analyte are known to a person skilled in the art and can be used in the devices and methods according to the invention.

Another typical embodiment of the present invention is shown in FIG. 2 as an alternative to the test element shown in FIG. 1. The partial views in FIGS. 2A to 2D in turn give a spatial impression of the test element according to the invention. The test element shown contains according to the invention a channel (5) capable of capillary liquid transport which is formed by an inert support (1), two intermediate layers (2) and the network (3). In this case the two intermediate layers (2) form the lateral boundaries, the support (1) forms the bottom surface and the network (3) forms the cover of the capillary channel (5). In this embodiment, the support (1) can be in a planar form such that no additional manufacturing or working steps are necessary to introduce a depression into it. This can result in much simpler and cheaper manufacturing process for such test elements according to the invention. In this case, the geometry of the capillary channel (5) can be determined by the dimensions of the intermediate layers (2). Thus, the height of the capillary channel (5) which substantially determines its capillary properties can be adjusted by the layer thickness of the intermediate layer (2). The width of the capillary channel (5) which substantially determines its cross-section and, thus, its volume can be adjusted by the distance between the two intermediate layers (2). Hence, this determines the volume of the liquid sample in the capillary gap (5) and, thus, this geometric parameter can be used for volumetric metering and allows an analyte determination to be carried out with the highest possible accuracy. The length of the capillary channel (5) can be determined by the length of the intermediate layers (2) which substantially determines the length of the transport path of the liquid sample from the sample application area to the detection element (4) and, thus, the distance from the site of application to the detection site which in turn plays a decisive role for the simplest and most hygienic handling. In this case, the geometric parameters length, width and height do not necessarily have to fulfil the functions described here but rather it is also possible that some individual parameters adopt the functions of other parameters or can also simultaneously fulfil several functions. Thus, a suitable selection of the height of the intermediate layers (2) may not only be used to influence its capillary activity but also to adjust the volume and, thus, the dosing of the liquid sample.

In yet another typical embodiment, the intermediate layers (2) can be manufactured from double-sided adhesive tapes. On the one hand their geometric dimensions enable an exact geometric definition of the capillary channel (5) and at the same time they enable a spatial connection of the individual components of the capillary gap (5). For this purpose, the two double-sided adhesive tapes are firstly glued onto the support (1) as intermediate layers (2) at an exactly defined distance from one another. Subsequently, after removing any protective foils from the tape, the network (3) is glued to the double-sided adhesive tapes by application and pressing in such a manner that a capillary channel (5) is formed. This embodiment allows a very inexpensive and simple manufacture of such test elements according to the invention.

FIG. 3 shows a schematic diagram of several views (FIGS. 3A to 3D) of another embodiment of a test element according to the invention. This embodiment has an intermediate layer (2) which is comprised of a special double-sided adhesive tape. This design is used in combination with the network (3) that is applied at the appropriate site typically to form a sample application area (7) and a vent hole (8) which ensures a problem-free and complete filling of the capillary gap (5) with the sample liquid. The intermediate layer (2) can be shaped by punching or cutting. Due to the design of the sample application area (7) and the vent hole (8), the network (3) does not necessarily cover the entire basal area of the support (1) or of the intermediate layer (2), but rather it allows a part of the support (1) and the intermediate layer (2) mounted thereon uncovered especially in the sample application area (7). Areas of the intermediate layer (2) that are not covered by the network can be provided with a cover. This can be advantageous when using a double-sided adhesive tape as an intermediate layer (2) since the adhering areas outside the network (3) are covered. For sample application one or more drops of the sample liquid are applied to the sample application area (7) which due to the design of the sample application area (7) immediately come into contact with the capillary gap (5) so that the sample liquid is immediately transported in the capillary gap (5) by means of capillary forces and is thus immediately transported to the detection element (4).

The vent hole (8) can also be specially designed. Thus, in order to reduce the consumption of material it may be appropriate to end the network (3) and, thus, the capillary channel (5) relatively directly after the detection element (4) as shown in this embodiment. Furthermore, in this embodiment the detection element (4) also covers the network (3) in areas which are no longer directly above the capillary channel (5). In such cases the detection element (4) is typically designed such that it has properties or structures which can distribute the liquid flowing out of the capillary channel (5) over the entire detection element (4). Thus, the detection element (4) can contain, for example, fleece-like structures or papers. Furthermore, in this embodiment the detection element (4) is immobilized on the network (3) by two attachment elements (6). These attachment elements (6) are at least attached to two sides of the detection element (4) and position it in a particular position on the network (3). Another function of these attachment elements (6) is to enable the underside of the detection element (4) to make contact with the upper side of the network (3) in such a manner that it allows the liquid sample to be transported from the capillary channel (5) across the network (3) into the detection element (4) by means of capillary forces. This can be achieved by pressing the detection element (4) onto the network (3). In this case the attachment elements (6) can, for example, be designed such that they cover the edge areas of the detection element (4) and, thus, attach it to the network (3).

In yet another embodiment, the detection element (4) can be immobilized on the network (3) by applying liquid hot-melt adhesive to two edge regions of the detection element (4) and the neighbouring areas of the network (3). After cooling, the hot-melt adhesive fixes the position of the detection element (4) on the network (3) and, on the other hand, makes the contact between the detection element (4) and network (3) that is necessary for liquid transfer by means of contact pressure towards the network (3).

FIG. 4 shows still another embodiment of a multiparameter test support (1) according to the invention with several detection elements (4) located behind one another and a sample application area (7) and vent hole (8). FIG. 4A is a top-view of the test element. FIGS. 4B to 4D each show cross-sections along the axis A-A', B-B' and C-C' respectively.

The test element shown here has three detection elements (4) as an example which are separated from one another by attachment elements (6). However, test elements are also encompassed which have two, or more than three detection elements (4). In this case the detection elements (4) can detect the same analyte but typically detection elements are combined in the form of a multiparameter test element which detect different analytes. The attachment elements (6) typically have liquid-repellent, more particularly, hydrophobic properties, and directly border the detection elements (4). As a result they restrict the transport of the liquid in such a manner that liquid can only be transported from the capillary gap (5) across the network (3) into the respective detection element (4) without a lateral mixing of the individual liquid segments and, thus, carry-over problems occurring. Such a multiparameter test element can be more typically used to detect analytes in the form of a panel test in a diagnostic context. For example, a multiparameter test element according to the invention can be used to determine parameters which are associated with an increased risk or presence of cardiovascular diseases. Such parameters are, for example, total cholesterol, HDL cholesterol, LDL cholesterol or triglycerides. A combination of detection elements for cholesterol, HDL cholesterol and triglycerides is more typical, which are arranged in the form of a panel test behind one another on the test element.

Another subject matter of the invention is the use of an analytical test element according to the invention to determine an analyte in a liquid.

Furthermore, the invention also concerns a method for determining an analyte in a liquid sample, typically a body fluid such as blood, plasma, serum, urine, saliva, sweat, etc., with the aid of an analytical test element according to the invention. The invention concerns a method for determining an analyte in a liquid with the aid of an analytical test element according to the invention in which the liquid is brought into contact with the test element typically in a sample application area, the liquid is transported by capillary forces in the channel capable of liquid transport at least up to the area of the detection element, is transported in the area of the detection element through the network to the detection element and there undergoes an analyte-specific detection reaction with the reagents contained in the detection element and, in particular, one that can be observed visually or by an optical apparatus typically by reflection photometry by means of which the presence and optionally the amount of the analyte to be determined can be deduced.

In this method the liquid sample is firstly contacted with the test element typically at a specially formed sample application opening. The sample liquid is transported by capillary forces in the channel capable of capillary liquid transport. It is transported at least up to the areas of the capillary gap which are opposite to the detection element. In these areas the liquid sample can penetrate into the detection element across the network and undergo an analyte-specific detection reaction with the reagents contained in the detection element and, in particular, a detection reaction that can be observed visually or by an optical apparatus, typically by reflection photometry. This can be used to deduce the presence or absence and optionally the amount of the analyte to be determined.

In order that the invention may be more readily understood, reference is made to the following examples, which are intended to illustrate the invention, but not limit the scope thereof.

EXAMPLES

Example 1

Production of an Analytical Test Element (cf. FIG. 4)

A double-sided adhesive tape having a thickness of 200 µm is glued a few millimeters from the edge onto a 350 µm thick support foil made of polyethylene terephthalate (Melinex®, ICI, Frankfurt am Main, Germany) which was previously hydrophilized by treatment with dioctyl sodium sulfosuccinate (2% in ethanol, Merck KgaA, Darmstadt, Germany). The support foil has a length of 75 mm and a width of 5 mm. The adhesive tape has a length of 35 mm and also a width of 5 mm. In addition, one end of the adhesive tape which corresponds to the subsequent vent hole has a central punched hole of 2 mm width and 15 mm to 25 mm length which defines the dimensions of the capillary channel. A specially shaped sample application area typically adjoins the side of the punched hole opposite to the vent hole. This is formed by an oval punched hole of 6 mm length and 3 mm width. The length of the punched hole can be selected to be slightly larger than the desired length of the capillary-active channel which is determined by its cover in order to ensure the channel is vented while it is filled with sample liquid. A network of 5 mm width is glued onto the adhesive tape over the length of the capillary gap, i.e., from the sample application area to the vent hole. The network is composed of monofilament PET fabric (Sefar Petex 07-98/34 from Sefar AG, Rueschlikon, Switzerland). In order to improve the inventive transport properties for liquids, the network is additionally hydrophilized by impregnation with 0.1% dioctyl sodium sulfosuccinate (Merck, KgaA, Darmstadt, Germany). The areas of the punched out adhesive tape that are not covered by the network in the area of the sample application site are additionally covered by an inert cover foil. Three detection elements are fastened by hot-melt adhesive on the network which is connected to the support foil by the adhesive tapes such that liquid can be transported from the capillary channel across the network to the detection elements. For this purpose the hot-melt adhesive is applied in a liquid form to the sides of the detection elements that are perpendicular to the capillary channel and flows at least partially into the network. After the hot-melt adhesive has hardened, the detection elements are attached to the network in such a manner that a lateral movement of the detection elements is prevented. Furthermore, the attachment with hot-melt adhesive presses the detection elements against the network such that the liquid sample can flow from the capillary channel across the network into the detection element. In this connection particular care must be taken that no hot-melt adhesive flows through the network into the capillary gap since this would otherwise affect or even completely stop the transport of sample liquid in the capillary gap. The detection elements contain the reagents necessary for the detection reactions of the respective analyte and optionally auxiliary substances. Such a test element can be particularly suitable as a multiparameter test element for determining parameters which are associated with an increased risk or presence of cardiovascular diseases. For this purpose detection elements for HDL cholesterol, cholesterol and triglycerides are immobilized behind one another on the network. Such detection elements are for example described in the data sheets for Reflotron® HDL cholesterol, Reflotron® cholesterol, and Reflotron® triglycerides (all from Roche Diagnostics, Mannheim, Germany). In this connection the hot-melt adhesive is not only used to attach the detection elements but also has the effect that no liquid from one detection element can reach a neighbouring detection element and, thus, minimizes carry-over problems. The detection elements can, for example, have a width of 5 mm and a length of about 4 mm. The cross-pieces of hot-melt adhesive for attaching and separating the individual detection elements typically have a width of 5 mm and a length of 1 to 2 mm.

Example 2

Measurement of Lipid Parameters with the Aid of the Test Element From Example 1

The sample application area of the test element from Example 1 is contacted with one drop of blood. The capillary of the test element automatically and uniformly fills with sample liquid within 3-5 seconds. In the areas of the detection elements the sample liquid flows across the network essentially simultaneously into the detection elements which starts the respective detection reaction. A colour development in the detection element is visible within a few seconds which can be used after completion of the measuring time to determine the analyte. This measuring time is, for example, about 135 sec. for a HDL cholesterol determination according to the Reflotron® HDL cholesterol method, about 135 sec. for a cholesterol determination according to the Reflotron® cholesterol method, and about 180 sec. for a triglyceride determination according to the Reflotron® triglyceride method. The intensity of the colour of the detection element can be determined by reflection photometry. This colour intensity is correlated with the concentration of the analyte in the sample.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in an embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analytical test element for determining at least one analyte in a liquid, the analytical test element comprising:
   a support having a first side;
   at least one intermediate layer provided over a portion of the first side of the support;
   a hydrophilic network comprising a non-absorbent fabric material having mesh interspaces with mesh widths of about 10 µm to about 500 µm, the hydrophilic network having a first side, a second side opposite the first side of the hydrophilic network, and a channel-covering portion, the first side of the hydrophilic network facing the first side of the support, the hydrophilic network provided over at least a portion of the at least one intermediate layer such that the channel-covering portion, lateral surfaces of the portion of the at least one intermediate layer underneath the hydrophilic network, and the first side of the support together define a capillary channel between the support and the hydrophilic network; and
   at least one capillary-active detection element having a contact side, the at least one capillary-active detection element provided over at least a portion of the hydrophilic network such that the contact side faces the second side of the hydrophilic network, such that the entire contact side is in direct contact with the second side of the hydrophilic network and defines a contact zone of the hydrophilic network and the at least one capillary-active detection element, and such that at least a portion of the contact side contacts the channel-covering portion of the hydrophilic network and defines a fluidic-connection portion of the contact side,
   wherein the liquid can be transported through the hydrophilic network only where the channel-covering portion of the hydrophilic network contacts the fluidic-connection portion of the contact side of the at least one capillary-active detection element, and wherein the contact zone comprises continuous capillary-active spaces from the capillary channel to the at least one capillary-active detection element through the mesh interspaces of the hydrophilic network.

2. The analytical test element of claim 1, wherein the non-absorbent fabric material is a monofilament fabric.

3. The analytical test element of claim 1, wherein the non-absorbent fabric material comprises polyethylene terephthalate.

4. The analytical test element of claim 3, wherein the polyethylene terephthalate is hydrophilized.

5. The analytical test element of claim 4, wherein the polyethylene terephthalate is hydrophilized with a wetting agent.

6. The analytical test element of claim 5, wherein the wetting agent is selected from dioctyl sodium sulfosuccinate, oleoyl sarcosine acid, or combinations thereof.

7. The analytical test element of claim 1, wherein the hydrophilic network has a mesh width from about 20 µm to about 300 µm.

8. The analytical test element of claim 1, wherein the hydrophilic network has a mesh width from about 50 µm to about 150 µm.

9. The analytical test element of claim 1, wherein the hydrophilic network has a fiber diameter from of between about 10 µm to about 300 µm.

10. The analytical test element of claim 1, wherein the hydrophilic network has a fiber diameter from about 30 µm to about 150 µm.

11. The analytical test element of claim 1, wherein the hydrophilic network has a fiber diameter from about 50 µm to about 100 µm.

12. The analytical test element of claim 1, wherein the hydrophilic network has a thickness from about 10 µm to about 500 µm.

13. The analytical test element of claim 1, wherein the hydrophilic network has a thickness from about 20 µm to about 300 µm.

14. The analytical test element of claim 1, wherein the hydrophilic network has a thickness from about 50 µm to about 150 µm.

15. The analytical test element of claim 1, wherein the capillary-active detection element comprises one or more reagents employed in the detection reaction of the analyte in the liquid.

16. The analytical test element of claim 1, wherein the capillary-active detection element comprises filter structures for particulate sample components.

17. The analytical test element of claim 1, wherein a plurality of individual capillary-active detection elements are arranged on the second side of the hydrophilic network facing away from the capillary channel, said individual detection elements being spatially separated from one another by liquid-impermeable boundaries.

18. The analytical test element of claim 1, wherein the detection element can detect the presence, absence, or concentration of total cholesterol, HDL cholesterol, LDL cholesterol, triglycerides, glucose, glycosylated haemoglobin, total haemoglobin, or a combination thereof.

19. The analytical test element of claim 1, wherein the detection element detects the presence, absence, or concentration of total cholesterol, HDL cholesterol, LDL cholesterol, triglycerides, glucose, glycosylated haemoglobin, total haemoglobin, or a combination thereof in whole blood or a blood product derived therefrom.

20. The analytical test element of claim 19, wherein the blood product is serum or plasma.

21. A method for determining at least one analyte in a liquid, the method comprising:
   a) contacting a liquid sample with an analytical test element, the test element comprising
      a support having a first side;
      at least one intermediate layer provided over a portion of the first side of the support;
      a hydrophilic network comprising a non-absorbent fabric material having mesh interspaces with mesh widths of about 10 μm to about 500 μm, the hydrophilic network having a first side, a second side, and a channel-covering portion, the first side of the hydrophilic network facing the first side of the support, the hydrophilic network provided over at least a portion of the at least one intermediate layer such that the channel-covering portion, lateral surfaces of the portion of the at least one intermediate layer underneath the hydrophilic network, and the first side of the support together define a capillary channel between the support and the hydrophilic network; and
      at least one capillary-active detection element having a contact side, the at least one capillary-active detection element provided over at least a portion of the hydrophilic network such that the contact side faces the second side of the hydrophilic network, such that the entire contact side is in direct contact with the second side of the hydrophilic network and defines a contact zone of the hydrophilic network and the at least one capillary-active detection element, and such that at least a portion of the contact side contacts the channel-covering portion of the hydrophilic network and defines a fluidic-connection portion of the contact side,
      wherein the liquid can be transported through the hydrophilic network only where the channel-covering portion of the hydrophilic network contacts the fluidic-connection portion of the contact side of the at least one capillary-active detection element, and wherein the contact zone comprises continuous capillary-active spaces from the capillary channel to the at least one capillary-active detection element through the mesh interspaces of the hydrophilic network;
   b) transporting the liquid in the capillary channel by capillary forces at least as far as the area of the capillary-active detection element;
   c) transporting the liquid from the capillary channel across the hydrophilic network to the capillary-active detection element;
   d) reacting the liquid with at least one reagent in the capillary-active detection element; and
   e) observing an indicator of the presence, absence, or concentration of the analyte.

22. The analytical test element of claim 1, wherein the capillary channel further comprises a sample application area at a first end of the capillary channel, a vent hole at a second end of the capillary channel opposite the first end, or both.

23. An analytical test element for determining at least one analyte in a liquid, the analytical test element comprising:
   a support having a first side with a recess defined therein;
   a hydrophilic network comprising a non-absorbent fabric material having mesh interspaces with mesh widths of about 10 μm to about 500 μm, the hydrophilic network having a first side, a second side opposite the first side of the hydrophilic network, and a channel-covering portion, the first side of the hydrophilic network facing the first side of the support, the hydrophilic network provided over at least a portion of the first side of the support, the channel-covering portion covering at least a portion of the recess so as to define a capillary channel between the support and the channel-covering portion; and
   at least one capillary-active detection element having a contact side, the at least one capillary-active detection element provided over at least a portion of the hydrophilic network such that the contact side faces the second side of the hydrophilic network, such that the entire contact side is in direct contact with the second side of the hydrophilic network and defines a contact zone of the hydrophilic network and the at least one capillary-active detection element, and such that at least a portion of the contact side contacts the channel-covering portion of the hydrophilic network and defines a fluidic-connection portion of the contact side,
   wherein the liquid can be transported through the hydrophilic network only where the channel-covering portion of the hydrophilic network contacts the fluidic-connection portion of the contact side of the at least one capillary-active detection element, and wherein the contact zone comprises continuous capillary-active spaces from the capillary channel to the at least one capillary-active detection element through the mesh interspaces of the hydrophilic network.

24. The analytical test element of claim 23, wherein the non-absorbent fabric material is a monofilament fabric.

25. The analytical test element of claim 23, wherein the non-absorbent fabric material comprises polyethylene terephthalate hydrophilized with a wetting agent selected from the group consisting of dioctyl sodium sulfosuccinate, oleoyl sarcosine acid, and combinations thereof.

* * * * *

UNITED STATES PATENT AND TRADEMARK OFFICE
CERTIFICATE OF CORRECTION

| | | |
|---|---|---|
| PATENT NO. | : 7,820,451 B2 | Page 1 of 1 |
| APPLICATION NO. | : 10/959734 | |
| DATED | : October 26, 2010 | |
| INVENTOR(S) | : Michael Brauner | |

It is certified that error appears in the above-identified patent and that said Letters Patent is hereby corrected as shown below:

Col. 16, Line 22, "network or the" should read -- network (3) or the --

Col. 22, Claim No. 9, Line 25 "diameter from of between" should read -- diameter from --

Signed and Sealed this
Tenth Day of May, 2011

David J. Kappos
*Director of the United States Patent and Trademark Office*